United States Patent [19]

Petersen

[11] 4,125,551
[45] Nov. 14, 1978

[54] PROCESS FOR PRODUCING SILYLPHOSPHATES

[75] Inventor: Louis P. Petersen, Latham, N.Y.

[73] Assignee: General Electric Company, Waterford, N.Y.

[21] Appl. No.: 877,053

[22] Filed: Feb. 13, 1978

[51] Int. Cl.² .............................................. C07F 7/08
[52] U.S. Cl. ...................... 260/448.2 E; 260/448.2 N
[58] Field of Search ................................. 260/448.2 E

[56] References Cited
U.S. PATENT DOCUMENTS 2,951,860  9/1960  Plueddemann ............... 260/448.2 E
4,008,261  2/1977  Brown et al. ................. 260/448.2 E Primary Examiner—Paul F. Shaver
Attorney, Agent, or Firm—Philip E. Koltos; John L. Young; Frank L. Neuhauser

[57] ABSTRACT

An improved process for producing silyl phosphates in the reaction of phosphoric acid with the linear low molecular weight polysiloxane alone or in combination with cyclicpolysiloxanes where there is present in the composition as a catalyst from 1.2 to 180% by weight of the total composition of a silylphosphate in which the phosphoric acid equivalency in the reaction mixture is from 0.36 to 1.80%.

18 Claims, No Drawings

PROCESS FOR PRODUCING SILYLPHOSPHATES

BACKGROUND OF THE INVENTION

The present invention relates to silylphosphates and more particularly the present invention relates to an improved process for producing silylphosphates wherein the reaction ingredients there is present a catalytic amount of a silylphosphate to initiate the reaction.

The compositions of diorganopolysiloxane polymers is well known. Such polymers in the case of heat vulcanizable silicone rubber compositions comprise taking a high molecular weight diorganopolysiloxane gum, incorporating filler into it and other additives, and then curing the gum in the presence of a peroxide catalyst at elevated temperatures.

In the case of room temperature vulcanizable silicone rubber compositions, the process for forming them comprises taking a silanol-terminated diorganopolysiloxane polymer, a filler, a cross-linking agent such as, an acetoxy or alkoxy functional silane, and a catalyst such as a metal salt of a carboxylic acid or a titanium chelate in the case of alkoxy functional silanes, wherein the ingredients are mixed in anhydrous conditions and when exposed to atmospheric moisture cures to a silicone elastomer. Such a room temperature vulcanizable silicone rubber composition is known as a one-component system or a one-package system since all of the ingredients are incorporated into the composition and all that is needed to cure the composition is to expose it to atmospheric moisture.

There is also known two-component room temperature vulcanizable silicone rubber compositions. Such compositions comprise a silanol-terminated diorganopolysiloxane polymer and a filler wherein the filler and silonal material are packaged separately in a first component. Then in the second component, that is packaged separately, there is present an alkyl silicate or alkyl orthosilicate and a metal salt of carboxylic acid. When it is desired to cure the composition the two components are mixed and applied and at room temperature to cure to a silicone elastomer. Such a composition which is a two-component room temperature vulcanizable silicone rubber composition will cure either in the presence or absence of atmospheric moisture. The main ingredient in either the heat curable composition or the room temperature vulcanizable silicone composition is the diorganopolysiloxane polymer which polymer is a viscous mass at room temperature or at elevated temperatures, but which cross-links during cure of the above composition to form a silicone elastomer.

The process for forming such diorganopolysiloxane polymers is also well known. Such a process generally comprises taking diorganodichlorosilanes and hydrolyzing them where the organo groups can be any monovalent hydrocarbon radical or halogenated monovalent hydrocarbon radical to form a mixture of low molecular weight diorganopolysiloxane polymers and cyclicsiloxanes.

Accordingly, to proceed further in the process, there is added a cracking catalyst to such a hydrolyzate such as, potassium hydroxide and the resulting mixture is heated at elevated temperatures, that is, temperatures above 100° C., to preferentially convert most of the low molecular weight linear polysiloxanes and cyclicsiloxanes to cyclotetrasiloxanes. It can be appreciated in the initial hydrolyzate and even during the cracking process that there are other cyclicpolysiloxanes such as, cyclotrisiloxanes, cyclopentasiloxanes, cyclohexylsiloxanes, and etc. However, it has been found for non-fluorinated polymers that the most desirable cyclopolysiloxane for the formation of linear diorganopolysiloxane polymers is a cyclotetrasiloxane. Accordingly, after there has been obtained sufficient conversion of the hydrolyzate to the cyclotetrasiloxanes such cyclotetrasiloxanes are collected in essentially pure form by distillation procedures.

In accordance with the desired type of substitution that is desired in the final linear diorganopolysiloxane polymer, such cyclotetrasiloxanes are taken and then there is added to them from 5 to 500 parts per million of a strong alkali metal hydroxide as a catalyst. The preferred catalyst is potassium hydroxide, however, sodium hydroxide can be used in certain instances. In certain cases such as with fluoro-substituted cyclotetrasiloxanes there can also be used a stronger alkali hydroxide catalyst such as, for instance, cesium hydroxide. However, for the preparation of other than fluorosubstituted linear diorganopolysiloxane polymers, the cyclotetrasiloxanes are taken, there is added into them the appropriate amount of alkali metal hydroxide, and there is also added to them the appropriate amount of chain-stoppers such chain-stoppers being low molecular weight linear triorganopolysiloxane polymers. An example of a suitable chain-stopper is, for instance, hexamethyldisiloxane, octamethyltrisiloxane and etc.

Accordingly, in the case for the preparation of linear diorganopolysiloxane polymers the above mixture is then heated at temperatures above 100° C., and preferably at temperatures above 150° C. to form a linear diorganopolysiloxane polymer. It should be noted in such reaction, which is known as an equilibration reaction, that the rings of the cyclopolysiloxanes are broken and the cyclopolysiloxanes react with each other to form a linear diorganopolysiloxane polymer. However, when about 85% of the cyclotetrasiloxanes have been converted to a linear diorganopolysiloxane polymer, it has been found that no more of the linear diorganopolysiloxane polymer is formed. Accordingly, at about the 85% conversion level the reaction is usually terminated by cooling the reaction mixture, neutralizing the alkali metal hydroxide catalyst with an acid, and then venting off or stripping off the unreacted cyclics, which cyclics can be recycled in another equilibration reaction. It should be noted that the molecular weight and viscosity of the final linear diorganopolysiloxane polymer that is formed as a result of the above reaction will depend on the amount of chain-stoppers that is utilized in the reaction mixture since this will basically control the average molecular weight of the polymers that are formed.

To produce a silanol-terminated diorganopolysiloxane polymer basically the same reaction is used except for a chain-stopper there is utilized low molecular weight silanol-terminated diorganopolysiloxane polymers or water.

One important part of this process for forming such linear diorganopolysiloxane polymers, whether silanol-terminated or triorganosilyl-terminated, is the neutralization of the basic catalyst that is utilized in the equilibration reaction. It is desired that the catalyst be neutralized since if it is not neutralized, even at room temperature, it will cause reversion of the linear diorganopolysiloxane polymer to the corresponding cyclotetrasiloxanes over a period of time. In addition, if the alkali metal hydroxide catalyst is not neutralized the cured elastomer that is formed from such a polymer will not have as good physical properties as would be desired and would be susceptible to degradation due to reversion again in the presence of heat or high humidity.

Many known types of acids are known to have been utilized for such neutralization procedures. However, one difficulty with strong acids such as hydrochloric and sulfuric acid is that care has to be taken that the amount of acid that is added is exactly the appropriate amount to carry out the neutralization. It has been found that excess acid in such linear diorganopolysiloxane polymers will cause degradation of the polymer similar to the type that is obtained when there is present excess base or excess alkali metal hydroxide in the linear diorganopolysiloxane polymer. Accordingly, the exact neutralization of the alkali metal hydroxide with a strong acid is very difficult and time consuming to carry out in a large plant batch reaction mixture.

The same kind of difficulty is experienced with mild acids such as, acetic acid. In addition, recently there evolved a semi-continuous or continuous process for the production of linear diorganopolysiloxane polymers. Accordingly, in such processes it becomes very important to have a neutralizing agent which will quickly and continuously neutralize the alkali metal hydroxide in the equilibration reaction mixture without necessitating the weighing out of exact amounts of neutralizing agent for the neutralization reaction. Accordingly, it was highly desirable to utilize a buffering type of acid for neutralizing the alkali metal hydroxide in the foregoing equilibration reactions. An example of a good buffering acid for the neutralization reaction of alkali metal hydroxides is phosphoric acid. Such an acid has the appropriate buffering action with alkali metal hydroxides and as such exact quantities of it do not have to be metered out in the reaction mixture to completely neutralize the alkali metal hydroxide without making the polymer strongly acidic. Another triprotic acid having this property such as, for instance, is arsenic acid but arsenic acid is undesirably toxic and has oxidizing and reduction properties that make it undesirable.

Phosphoric acid is cheap and non-toxic and accordingly is highly desirable as a neutralizing agents in the foregoing equilibration reactions. However, phosphoric acid has one disadvantage, that is, it is not soluble in the linear diorganopolysiloxane polymer or in the cyclotetrapolysiloxanes. Accordingly, because of its limited solubility it takes time for it even with good agitation to mix with the alkali metal hydroxide so as to neutralize it in an equilibration reaction mixture. This disadvantage which is noticeable for batch type of equilibration reactions causes even more of a problem in its use in the neutralization of continuous polymerization reactions. Accordingly, because of its limited solubility phosphoric acid is utilized with difficulty in neutralizing alkali metal hydroxide catalysts in continuous equilibration reactions for the formation of linear diorganopolysiloxane polymers.

Accordingly, it was highly desirable to have a soluble form of phosphoric acid so that it could be utilized as a neutralizing agent in equilibration reactions for forming linear diorganopolysiloxane polymers whether such processes were continuous or batch-wise. Such a soluble form of silyl phosphates is disclosed in the patent application of Razzano, Ashby, Peterson, Docket 60SI-7, entitled "Silyl Phosphates as Neutralizing Agents for Alkali Metal Hydroxides", Ser. No. 854,562, filed on Nov. 25, 1977. While such silyl phosphates are advantageous for both the batch and continuous neutralization of alkali metal hydroxides they are formed only with difficulty from phosphoric acid. The basic process for producing such silyl phosphates is to react low molecular weight diorganopolysiloxane polymers with phosphoric acid at elevated temperatures so as to form the desired silyl phosphate product. Another process, and more desirable, which produced a soluble form of silyl phosphate was the reaction of a linear diorganopolysiloxane polymer of low molecular weight with a cyclotetrasiloxane and phosphoric acid at elevated temperatures. However, in both such reactions of polysiloxanes with phosphoric acid it was found that the reaction (even at elevated temperatures) would not initiate for anywhere from 30 minutes to 2 hours and then would suddenly initiate with a very rapid and uncontrollable evolution of water which was vaporized at the reaction temperature with the rate of formation of water vapor causing the reaction mixture to boil out of the reaction vessel. Accordingly, it was highly desirable to have a reaction of the polysiloxanes in phosphoric acid in which the reaction initiated quickly and proceeded smoothly at a rapid rate and such that the reaction was not violent.

Accordingly, it is one object of the present invention to provide for an efficient process for producing silyl phosphates from phosphoric acid.

It is another object of the present invention to provide for a catalyst for the reaction of phosphoric acid with polysiloxanes such that the reaction will initiate promptly and proceed smoothly and under control.

It is an additional object of the present invention to provide for an efficient process for the production of silyl phosphates by the reaction of phosphoric acid with polysiloxanes such that the reaction initiates quickly and proceeds smoothly in a short period of time.

These and other objects of the present invention are accomplished by means of the disclosure set forth hereinbelow.

SUMMARY OF THE INVENTION

There is provided by the present invention and in accordance with the above objects an improved process for producing silyl phosphates comprising reacting (1) from 1 to 30 parts of phosphoric acid with (2) per 100 parts of a polysiloxane of the formula,

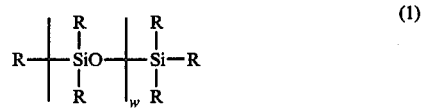

where R is a monovalent hydrocarbon radical and $w$ varies from 1 to 100 in the presence of (3) from 1.2 to 180% by weight of the total composition of a silyl phosphate in which the phosphoric acid equivalency in the reaction mixture is from 0.36 to 1.80% and preferably from 0.36 to 0.60%.

There is also provided by the present invention, an improved process for producing silyl phosphates from phosphoric acid comprising reacting (1) from 1 to 30 parts by weight of phosphoric acid with (2) 1 to 50 parts by weight of a polysiloxane of the formula,

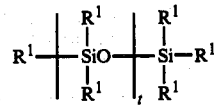

(2)

where $R^1$ is a monovalent hydrocarbon radical and $t$ varies from 1 to 100, and (3) 100 parts of a diorganocyclotetrasiloxane where the organo groups are monovalent hydrocarbon radicals in the presence of (4) from 1.2 to 180% by weight of the total composition of a silyl phosphate in which the phosphoric acid equivalency in the reaction mixture is from 0.36 to 1.80% and preferably from 0.36 to 0.60%. In both of the above reactions, irrespective of whether a cyclotetrasiloxane is present or not, the presence of a silyl phosphate in the foregoing quantities and more preferably at a concentration of 1.2 to 60% by weight providing 0.60 to 1.20% by weight of equivalent phosphoric acid results in a reaction which initiates quickly after the phosphoric acid is mixed with the polysiloxanes and in which there results a short reaction period without a violent reaction.

DESCRIPTION OF THE PREFERRED EMBODIMENT

The basic ingredients for producing the silyl phosphate of the instant invention as well as the ingredients for producing the silyl phosphate for neutralization in equilibration reaction comprises in one aspect, phosphoric acid and in a second aspect, a polysiloxane of the formula,

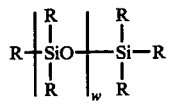

where R is a monovalent hydrocarbon radical and $w$ varies from 1 to 100. In the above formula, R may be any monovalent hydrocarbon radical or halogenated monovalent hydrocarbon radical such as, for instance, alkyl radicals of from 1 to 8 carbon atoms such as, methyl, ethyl and etc.; alkenyl radicals such as, vinyl, allyl, and etc.; halogenated alkyl radicals such as, fluoroalkyl radicals, specifically 3,3,3-trifluoropropyl radicals and etc.; cycloalkyl radicals such as, cyclohexyl, cycloheptyl, and etc.; and mononuclear aryl radicals such as, phenyl, methylphenyl and etc. Most preferably the R radical is selected from alkyl radicals of 1 to 8 carbon atoms and phenyl radicals. The above two reactants are not only the appropriate reactants for preparing silyl phosphates as neutralizing ingredients in equilibration reactions for alkali metal hydroxides in such reactions but also are the basic ingredients for producing the silyl phosphate catalyst of the instant case. Initially such silyl phosphate catalysts that are utilized within the scope of the instant invention may be produced by reacting the foregoing polysiloxane of the above formula with phosphoric acid without the catalyst to produce small quantities of the silyl phosphate and then utilizing such silyl phosphate product as a catalyst in the additional reactions of phosphoric acid with the polysiloxane. It should be noted in this instance that the silyl phosphates in the instant case may not only be utilized to neutralize alkali metal hydroxides in equilibration reactions, as discussed previously, but they may be utilized to neutralize alkali metal hydroxides in any instances where such alkali metal hydroxides are present in a mixture of silanes or siloxanes.

Accordingly, in the basic reaction for producing the silyl phosphates, generally from 1 to 30 parts by weight of phosphoric acid is reacted with 100 parts of the polysiloxane and more preferably from 3.0 to 20 parts by weight of the phosphoric acid is reacted with 100 parts by weight of the polysiloxane of Formula (1) above. It can be appreciated that the above concentrations of polysiloxane to phosphoric acid could vary within a wide range depending on the phosphoric acid equivalent it is desired that the silyl phosphate product have. Accordingly, a silyl phosphate product may have a phosphoric acid content of anywhere from 1 to 30% equivalency of phosphoric acid and more preferably has a phosphoric acid equivalency varying anywhere from 3 to 20%. The other necessary ingredient in the reaction for producing the silyl phosphate is a silyl phosphate catalyst in such quantity so as to provide 0.36 to 1.80% by weight of equivalent phosphoric acid to the total polysiloxane reaction mixture where there is used from 1.2 to 180% by weight of the total composition of a silyl phosphate which has the above phosphoric acid equivalency. It has been found that with the presence of a silyl phosphate as a catalyst in the reaction of the phosphoric acid with a polysiloxane of Formula (1) that the reaction is initiated more quickly, that is, in a matter of minutes after the phosphoric acid comes into contact with the polysiloxane of Formula (1), and that the reaction after that proceeds smoothly and quickly to produce the final silyl phosphate product.

Without the presence of the silyl phosphate catalyst, it has been found that the reaction may not initiate for a period of time varying anywhere from 1 hour to 2 hours and that the reaction after it has been initiated may proceed in a violent manner with possible eruption of the reaction vessel contents from the reaction vessel during the reaction. Accordingly, to solve this problem in the reaction of phosphoric acid with the polysiloxane of Formula (1), this problem can be eliminated by having in the reaction ingredients, that is, the combination of phosphoric acid and the polysiloxane of Formula (1), silyl phosphate in such concentration that from 0.36 to 1.80% by weight of equivalent phosphoric acid will be present in the reaction mixture. If less than 0.36% by weight of equivalent phosphoric acid from the silyl phosphate catalyst is present, then the reaction does not initiate quickly enough, that is, it will take about 30 minutes or so for the reaction to initiate with less than 0.36% by weight of equivalent phosphoric acid from the silyl phosphate catalyst in the reaction mixture. With more than 1.80% by weight of equivalent phosphoric acid from the silyl phosphate catalyst in the reaction mixture the reaction is initiated in a matter of minutes. However, no advantage is obtained by having excess silyl phosphate present resulting in excess of 1.80% by weight of equivalent phosphoric acid from the silyl phosphate catalyst. More preferably, the equivalent phosphoric acid concentration from the silyl phosphate catalyst varies anywhere from 0.36 to 0.60% by weight of the total composition from a total silyl phosphate concentration of generally 1.2 to 180% by weight in the reaction mixture and preferably 1.2 to 60% by weight of silyl phosphate based on the total reaction mixture wherein the silyl phosphate has the above phosphoric acid equivalency.

It should be noted that it is not important what structure the silyl phosphate catalyst has, that is, a silyl phosphate catalyst can have any structure in which there is a silyl phosphate compound and such a compound can be utilized in the reactions of the process of the instant case for producing silyl phosphate compounds. It is only necessary that the catalyst be the reaction product of phosphoric acid or a phosphorous oxy chloride compound or phosphorous oxy bromide compound and a polysiloxane of any type.

It is recognized that this process for preparing silyl phosphate is an equilibration process with the acidic equilibration catalyst being the silyl phosphate groups. As in any polysiloxane equilibration process, the resultant polymer does not have a single composition but is a statistical distribution of a variety of structures and molecular weights about a center point whose position is determined by the composition of the polymer. Some of the polymer's structure can be generally represented by the following formula,

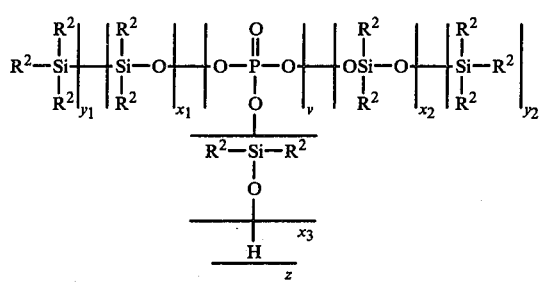

(3)

where the values of $v$, $y$, $x$ and $z$ are determined as follows:

$v$ is the concentration of phosphate groups;

$y_1 + y_2$ is the concentration of triorganosiloxane chain-stopper;

$x_1 + x_2 + x_3$ is the concentration of diorganosiloxanes; and $z$ is the concentration of hydroxyl groups which may be attached to a silicon or phosphorous atom resulting from incomplete removal of water during the process.

The radical $R^2$ is a monovalent hydrocarbon radical selected from the same radicals as R and $R^1$.

Thus, the properties of the silyl phosphate produced by this process is dependent upon composition of the starting mixture and not upon the starting material. Similar silyl phosphate may be produced starting with a linear polysiloxane as in Formula (1) or with a diorganocyclotetrasiloxane and a chain-stopper such as a hexaorganodisiloxane providing that the proportions of the diorganosiloxane, triorganosiloxane and phosphoric acid are constant.

The phosphate groups incorporated into the polysiloxane are recognized as the active catalyst form and effective catalyst activity results from estabishing an appropriate concentration of phosphate groups in the starting reaction solution. Since a silyl phosphate polysiloxane polymer can readily be prepared having a wide range of concentrations of phosphate groups, the amount of silyl phosphate polysiloxane required to effectively catalyze the reaction will need to be varied according to the phosphate concentration. The preferred catalyst concentration is that amount of silyl phosphate polysiloxane that will result in an equivalent phosphoric acid concentration of 0.36% to 1.80% by weight to the sum of the diorganosiloxanes and the triorganosiloxanes.

Irrespective of the formula or structure of the silyl phosphate catalyst, as long as it is a reaction product of a phosphate and a polysiloxane polymer the resulting silyl phosphate compound will act as a catalyst in the process of the instant case and activate the phosphoric acid to react with the polysiloxane of Formula (1) to produce a silyl phosphate neutralizing agent.

Utilizing the above silyl phosphate catalysts of the instant case in the reaction of phosphoric acid with the polysiloxane of Formula (1) in the foregoing concentrations, the reaction between the phosphoric acid and the polysiloxane initiates immediately and there is obtained a smooth reaction in which the total reaction time may vary anywhere from 15 minutes to 2½ hours. Preferably, the total reaction time varies from 30 minutes to 2 hours. Preferably, in the reaction of the phosphoric acid with the polysiloxane of Formula (1), a solvent is not utilized since solvents in which the phosphoric acid would be soluble in such as, water would not dissolve the polysiloxane polymer and visa-versa. If a solvent was available that would dissolve both the phosphoric acid and the polysiloxane then such a solvent could be utilized in the reaction to allow for a smoother reaction and to allow for more immediate contact of the phosphoric acid with the polysiloxane polymer formula of formula (1), to obtain the desired silyl phosphate reaction product of the instant invention.

Preferably, to carry out the reaction about 5 to 25% of the total phosphoric acid is placed initially in contact with the polysiloxane polymer of formula (1). Then the additional phosphoric acid is added while the mixture is agitated and heated during the reaction period over a period of time varying anywhere from 15 minutes to 2 hours or more. The continuous addition of phosphoric acid over a period of time allows for a smoother reaction period and also allows for a better contact of the phosphoric acid with the polysiloxane polymer of formula (1), so as to obtain the desired reaction. Such continuous addition of phosphoric acid, while desirable, is not necessary. The reaction of the instant case can be carried out by the batch-wise addition of the total amount of phosphoric acid to the polysiloxane polymer of formula (1) in the initial reaction mixture. However, the continuous addition of phosphoric acid is preferred over a period of time in order to have as smooth a reaction as possible, and in order to increase the contact of the phosphoric acid with a polysiloxane polymer in the reaction pot which results also in a faster reaction time for the silyl phosphate product that is obtained by the process of the instant case. To initiate the reaction of the instant case as well as by the use of the silyl phosphate catalyst of the instant case, as disclosed above, it is necessary to heat the reaction mixture to generally a temperature in the range of 140° to 225° C. and more preferably in a temperature range of 90° to 200° C. The reaction temperature may be closer to 140° level during the initial part of the reaction and rise to the 225° level at the end of the reaction period.

It is preferred during the reaction period that there be constant agitation of the reaction ingredients to insure intimate contact of the phosphoric acid, the silyl phosphate catalyst and the polysiloxane polymer of Formula (1). During such production of the silyl phosphate neutralizing agent and in accordance with the process of the instant case, water is formed. Accordingly, during such process and during the heating of the reaction ingredients to form the silyl phosphate neutralization agent product desirably the water that is formed is distilled off and collected. The more water that is collected the more the reaction has reached completion. It should be noted that it is desired that the final silyl phosphate product be kept away from water as much as possible since the presence of water will cause reversion of the silyl phosphate to the initial polysiloxane polymer and the phosphoric acid. Accordingly, during the reaction period and during such preferred continuous addition of phosphoric acid to the polysiloxane polymer of Formula (1) in the reaction pot, and during the heating of the reaction ingredients, water is continuously collected as it is formed until no more water can be collected at the selected reaction temperature. Not all of the water introduced with the 85% $H_3PO_4$ - 15% water solution and formed by the reaction of $H_3PO_4$ with polysiloxanes can be removed from the silyl phosphate. It has been found that a fully satisfactory silyl phosphate is obtained when approximately 70 to 80% of the theoretical water has been removed. It is recognized that the residual water remains in the product as silanol groups and/or hydroxyl groups on phosphorous. The amount of water left in the silyl phosphate has been found to decrease as the final reaction temperature is increased. At that point, the silyl phosphate product that results may be filtered to remove impurities and to result in the final silyl phosphate neutralizing agent. It should be noted that if water is not continuously distilled off during the reaction for producing the silyl phosphate neutralizing agent then at the end of the reaction period the water that has been formed may be distilled off as well to leave behind the silyl phosphate product of the instant case. The resulting silyl phosphate product may then be filtered again to remove impurities so as to result in the silyl phosphate neutralizing agent of the instant case.

It has been noted above that the basic process of the instant case involves the reaction of phosphoric acid with polysiloxanes of Formula (1) to form a silyl phosphate neutralizing agent. It has been found that in such reactions the silyl phosphate catalyst of the instant case is necessary to obtain a short reaction period and smooth reaction conditions. It has been found that when silyl phosphate catalysts are not utilized in such reactions, then such reactions have a prolonged reaction period and sometimes violent reaction conditions. It has also been found that the above is true only in the reaction of phosphoric acid with a polysiloxane. In the reaction of phosphorous oxy trichloride or phosphorous oxy tribromide with polysiloxanes the foregoing silyl phosphate catalyst is not needed since that reaction proceeds smoothly.

Accordingly, in addition to the above process, that is, the reaction of phosphoric acid with the polysiloxane of Formula (1) to produce a silyl phosphate neutralizing agent, there is encompassed within the instant case a reaction in which there is reacted (1) from 1 to 30 parts by weight of phosphoric acid with (2) 1 to 50 parts by weight of a polysiloxane of the formula,

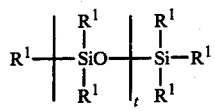

where $R^1$ is a monovalent hydrocarbon radical which is selected from the same types of radicals as was given above for the R radical of the compound of Formula (1), and $t$ varies from 1 to 100, and (3) from 100 parts by weight of a diorganocyclosiloxane where the organo groups are monovalent hydrocarbon radicals which are selected from the same type of radicals as given before for the R radical in the compound of Formula (1), wherein the above compounds are reacted in the presence of from 1.2 to 180% by weight of the total composition of a silyl phosphate in which the phosphoric acid equivalency in the reaction mixture is from 0.36 to 1.80% of a silyl phosphate wherein the foregoing silyl phosphate acts as a catalyst.

The cyclotetrasiloxane may have the formula,

where $R^3$ is a monovalent hydrocarbon radical which is selected from the same type of radicals as given previously for the definition of the R radical and $n$ varies from 3 to 10.

It should be noted that the only difference in the foregoing reactions set forth for producing the silyl phosphate product versus the reaction given previously is the presence of the cycloorganosiloxane. The presence of such a diorganocyclosiloxane and preferably cyclotetrasiloxane in the formulation mixture does not affect the reaction conditions and the carrying out of the process in any different manner from that disclosed above for the reaction of the polysiloxane of Formula (1) with the phosphoric acid.

Again, preferably, the cyclotetrasiloxane is mixed with the polysiloxane of Formula (2) in the reaction pot and there is added to that reaction mixture anywhere from 5 to 25% by weight of the total phosphoric acid and then the rest of the phosphoric acid is added continuously to the reaction mixture over most of the reaction period which may vary anywhere from 15 minutes to 1, 2 or 2½ hour periods. During such a reaction period, preferably the reaction mixture is again heated in the temperature range of 90° to 225° C. and more preferably in the range of 90° to 200° C. As stated previously, generally the reaction temperature will be more in the vicinity of 140° C. at the initial part of the reaction and then slowly increased to the 200° or 225° level.

In the reaction mixture it is preferred that the water that is formed during the production of the silyl phosphate be collected as the reaction progresses, such that when no more amount of water can be collected from the reaction mixture it can be assumed that the reaction has reached completion to produce the maximum amount of the silyl phosphate neutralizing agent of the instant case. However, in the alternative, no water need be collected from the reaction as it proceeds and when the reaction is terminated then at that time there can be stripped off all the water that has been formed to yield the desired silyl phosphate product of the instant case. This silyl phosphate product can then be filtered to remove undesired impurities and utilized as a neutralizing agent in equilibration reactions.

It should be noted that to obtain a silyl phosphate catalyst for the next reaction for forming a silyl phosphate, then a small amount of a silyl phosphate product can be segregated for this purpose. The rest of the silyl phosphate product is then ready to be utilized as a neutralizing agent in equilibration reactions.

The preferred concentration range of the silyl phosphate catalyst in this reaction, that is, the reaction of the polysiloxane of Formula (3) with phosphoric acid and cyclotetrasiloxane, is again 0.60 to 1.20% by weight of equivalent phosphoric acid and that the equivalency of the phosphoric acid of the silyl phosphate catalyst may vary anywhere from 1.0 to 30% and more preferably varies from 3% to 20% and such that the preferred concentration of the silyl phosphate in the reaction mixture based on the shown equivalency is from 1.2 to 60%.

In short, the silyl phosphate catalyst in either reaction may have, both in the previous reaction described in connection with the polysiloxane of Formula (1), or in the present reaction with the polysiloxane of Formula (2), any phosphoric equivalency within permissible limits.

Again, utilizing the foregoing reaction ingredients, that is, the polysiloxane of Formula (2), the cyclotetrasiloxanes and the phosphoric acid, there is generally obtained a reaction period varying anywhere from 15 minutes to 2½ hours and more preferably a reaction period varying from 30 minutes to 2 hours.

The silyl phosphates of this docket may also be utilized as catalysts in the presence of the instant case. However, it should be noted, as stated previously, that the use of a silyl phosphate catalyst in the reaction for production of a silyl phosphate neutralizing agent is limited to the case where phosphoric acid is one of the reactants and the polysiloxane is the other reactant, since it has been found that phosphoric acid will react only with difficulty with polysiloxanes to form silyl phosphates in accordance with the description given previously.

Accordingly, it has been found that the process for producing silyl phosphates from phosphoric acid and polysiloxanes is autocatalytic as explained previously. Although it is not understood fully the proposed mechanism for the autocatalysis it appears to be along the following lines. In the absence of catalytic amounts of silyl phosphate, 85% of phosphoric acid in water is insoluble in the polysiloxanes of formulas (1) and (2) and the cyclotetrasiloxanes so that any reaction must occur at the phosphoric acid siloxane interphase. It is postulated that the reaction rate may further be decreased by water competing with phosphoric acid for the polarized siloxane bonds. In contrast with a silyl phosphate catalyst present, the following type of phenomena may be occurring. For instance, the silyl phosphate in solution in a siloxane phase may maintain a significant concentration of polarized siloxane bonds so that the interfacial reaction need be only phosphoric acid reacting with the polarized polysiloxanes. In addition, the presence of silyl phosphate may possibly increase the polarity of the siloxane phase, thus, tending to increase the solubility of phosphoric acid in the polysiloxane and moving the reaction ingredients to a more homogeneous reaction mixture. Irrespective of what explanation is adopted and the above are just speculations, it has been found that the presence of a silyl phosphate catalyst in the reaction of phosphoric acid with either the polysiloxane of formula (1) or the polysiloxane of formula (2) with a cyclotetrasiloxane immeasurably improves the reaction conditions and shortens the reaction time for the production of the final silyl phosphate product.

The silyl phosphate neutralizing agent that is obtained by the process of the instant case has many uses in neutralizing alkali metal hydroxides and bases in siloxane solutions. Not only is the silyl phosphate soluble in polysiloxanes so as to quickly intermix the siloxanes to neutralize any alkali metal hydroxides that may be present, but further the silyl phosphate is a buffering type of neutralizing agent, that is, exact amounts do not have to be metered into the stream to be neutralized to obtain an exact neutralization of the alkali metal hydroxides without the possibility of their being formed excess acidity in the neutralizing mixture and without the necessity for back neutralization of the neutralization reaction mixture.

The silyl phosphate neutralizing agents of the instant case are especially suitable for neutralizing continuous polymerization reactions of silanol-terminated diorganopolysiloxane polymers. In such reactions, generally, and in a continuous manner, the appropriate cyclotetrasiloxanes are continuously equilibrated at temperatures above 150° C. while they are passed through a continuous reactor having the appropriate amount of potassium hydroxide therein which may be in the neighborhood of anywhere from 5 to 500 parts per million and more preferably, 5 to 100 parts per million of alkali metal hydroxide. In said stream there will also be the appropriate amount of chain-stopper which generally will be water. There also may be utilized as a chain-stopper in such equilibration reactions, a hydrolyzate that is obtained by hydrolyzing diorganodichlorosilanes and then removing the cyclics therefrom and utilizing such hydrolyzate with small amounts of water in it as a chain-stopper in the foregoing continuous equilibration reaction. Utilizing such a chain-stopper in the appropriate amounts and utilizing the potassium hydroxide in the foregoing quantities and equilibrating the appropriate cyclotetrasiloxanes at elevated temperatures in a continuous manner there will be continuously obtained a silanol diorganopolysiloxane polymer having a viscosity of anywhere from 1000 to 500,000 centipoise at 25° C. Accordingly, after such a polymer is formed and at the 85% equilibration level, then the catalyst may be continually neutralized by feeding into the stream continuously the foregoing desired quantities of silyl phosphate produced by the process of the instant case. Such continuous addition of the appropriate amounts of silyl phosphate into the continuous equilibration reaction stream will result in continuous neutralization of the alkali metal hydroxide catalyst in the stream such that all that has to be done at that point is to take the stream, strip the unreacted cyclics therefrom, and there results the silanol-terminated diorganopolysiloxane polymer that can be utilized in the formation of room temperature vulcanizable silicone rubber compositions.

Utilizing the same procedure, there can be obtained continuous equilibration reaction streams for producing triorganosilyl endstopped linear diorganopolysiloxane polymers. Irrespective of which continuous equilibration procedure is utilized to continuously produce linear diorganopolysiloxane polymers, the silyl phosphates produced by the process of the instant case can be utilized with advantage to continuously neutralize alkali metal hydroxides in such processes. The examples below are given for the purpose of illustrating the present invention. They are not given for any purpose of setting limits and bounds to the invention of the instant case, or for defining the scope of the instant invention and as set forth in the disclosure and claims. All weights are in grams and pounds.

EXAMPLES 1–10

There was prepared a silyl phosphate compound with various concentrations of a silyl phosphate catalyst in the initial reaction mixture. In some cases phosphoric acid was continuously fed to the reaction mixture for a period ranging from 75 to 100 minutes. In some cases, there was utilized a nitrogen purge and in some cases as well as the reaction conditions are set forth in Table II below.

TABLE II

| Ex. | Octylmethyl-cyclotetra-siloxane Lbs. | Hexamethyl-disiloxane Lbs. | Silyl Phosphate lbs. Catalyst | 85% $H_3PO_4$ lbs. | Theor Product | Theor $H_2O$ | Theor % $H_3PO_4$ | Feed Time Hrs. | Lbs. Prod. | % Yld. | Visc. | % $H_3PO_4$ |
|---|---|---|---|---|---|---|---|---|---|---|---|---|
| 11 | 317 | 28.3 | 19.3 | 55.0 | 411 | 21.1 | 11.9 | 3.4 | 366 | 89.1 | 383 | 11.8 |
| 12 | 317 | 28.3 | 19.3 | 55.0 | 411 | 21.1 | 11.9 | 2.6 | 409 | 99.5 | 430 | 11.8 |
| 13 | 317 | 28.3 | 19.3 | 55.0 | 411 | 21.1 | 11.9 | 2.8 | 411 | 100.0 | 428 | 11.2 | there was not. The reaction temperature which began at 150° C. in most cases, varied upwardly during the reaction period and the final temperature range of the reaction temperature being indicated in Table I below. The ingredients utilized to produce the silyl phosphate compounds as well as the presence and the amounts of silyl phosphate catalyst utilized in the reaction mixture are set forth in Table I below. In all cases where no silyl phosphate catalyst was utilized in the reaction mixture, the reaction did not initiate for a substantial period of time and then the reaction was violent. The specifics as to Examples 1-10, as well as the reaction conditions and reaction results is set forth in Table I below.

I claim:

1. An improved process for producing silyl phosphates comprising reacting (1) from 1 to 30 parts by weight of phosphoric acid with (2) 100 parts by weight of a polysiloxane of the formula,

where R is a monovalent hydrocarbon radical and $w$ varies from 1 to 100, in the presence of (3) from 1.2 to

TABLE I

| Ex. | Octylmethyl-cyclotetra-siloxane Gms | Hexamethyl-disiloxane (MM) Gms | 85% $H_3PO_4$ Gms | Silyl Phosph.** Gms | Theor. $H_3PO_4$ % | WT. % MM % | $H_3PO_4$ Feed | Feed Time Min. | Time To React Min. | Total React Time Min. | Final Temp. °C | $N_2$ Purge |
|---|---|---|---|---|---|---|---|---|---|---|---|---|
| 1 | 1102 | 97.9 | 200 | 0 | 12.4 | 7.40 | No | —* | 55 | 145 | 196 | No |
| 2 | 1102 | 97.9 | 200 | 0 | 12.4 | 7.40 | Yes | 60 | 100 | 240 | 190 | Yes |
| 3 | 1102 | 98.0 | 180 | 134 | 12.4 | 7.28 | Yes | 65 | 2 | 105 | 190 | Yes |
| 4 | 1000 | 200 ($MD_2M$) | 200 | 0 | 12.4 | 7.90 | No | —* | 250 | 280 | 190 | Yes |
| 5 | 1102 | 98 | 198 | 13 | 12.4 | 7.42 | Yes | 100 | 35 | 110 | 188 | Yes |
| 6 | 1102 | 98 | 194 | 40 | 12.4 | 7.43 | Yes | 90 | 15 | 100 | 175 | No |
| 7 | 1102 | 147 | 190 | 67 | 11.5 | 10.6 | Yes | 75 | 10 | 85 | 175 | No |
| 8 | 1102 | 49 | 190 | 67 | 12.3 | 4.0 | Yes | 90 | 15 | 100 | 175 | No |
| 9 | 1102 | 98 | 290 | 67 | 16.8 | 7.13 | Yes | 140 | 15 | 160 | 175 | No |
| 10 | 1102 | 98 | 90 | 67 | 6.31 | 7.79 | Yes | 40 | 10 | 70 | 175 | No |

*Run as pure batch reaction, all others with continuous feed of $H_3PO_4$.
**Silyl phosphate containing 12% equivalent $H_3PO_4$.

The above examples indicate that when silyl phosphate is not utilized as a catalyst in the reaction of phosphoric acid with polysiloxanes to produce silyl phosphates, that the reaction does not initiate for a long period of time and that when it does initiate that the reaction mixture undergoes a violent state.

EXAMPLES 11-13

The process procedure was to charge the octylmethylcyclotetrapolysiloxane, hexamethyldisiloxane and a silyl phosphate catalyst to the reactor and heat the mixture to 150° C. The agitator speed was set at approximately 180 rpm. The 85% phosphoric acid was then fed to the reactor at such a rate as to give it a 2.5 to 3 hour feed time. The reaction temperature was controlled in the range of 145° to 160° C. At that time water was collected from the azeotrope trap and periodically weighed to provide a record of the progress of reaction. During the last 30 minutes of phosphoric acid feed the reaction temperature was gradually increased to 170° C. Upon completion of phosphoric acid feed the reaction temperature was increased to 176° C. and the reaction held at that temperature for another 60 minutes. The reaction product was cooled to 50° to 60° C. and filtered to stainless steel drums through viscon paper. The product was then tested for viscosity and for phosphoric acid equivalency content. The results of these examples 180% by weight of the total composition of a silyl phosphate catalyst in which the phosphoric acid equivalency in the reaction mixture is from 0.36 to 1.80%.

2. The process of claim 1 wherein the silyl phosphate catalyst concentration is from 1.2 to 60% by weight such as to provide 0.36 to 0.60% by weight of phosphoric acid equivalency.

3. The process of claim 1 wherein the phosphoric acid equivalency of the silyl phosphate catalyst varies from 1 to 30%.

4. The process of claim 1 wherein the phosphoric acid equivalency of the silyl phosphate catalyst varies from 3 to 20%.

5. The process of claim 1 wherein the reaction period varies from 15 minutes to 2.5 hours.

6. The process of claim 5 wherein the reaction period varies from 30 minutes to 2 hours.

7. The process of claim 5 wherein the reactants are heated such that the reaction temperature is maintained in the range of 90° to 225° C. during the reaction period.

8. The process of claim 1 wherein during the reaction and thereafter the water that is formed is distilled off.

9. An improved process for producing silyl phosphates from phosphoric acid comprising reacting (1) from 1 to 30 parts by weight of phosphoric acid with (2) 1 to 50 parts by weight of a polysiloxane of the formula,

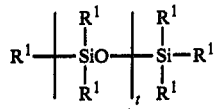

where $R^1$ is a monovalent hydrocarbon radical and $t$ varies from 1 to 100 and (3) with 100 parts by weight of a diorganocyclotetrasiloxane where the organo groups are monovalent hydrocarbon radicals, in the presence of (4) from 1.2 to 180% by weight of the total composition of a silyl phosphate catalyst in which the phosphoric acid equivalency in the reaction mixture is from 0.36 to 1.80%.

10. The process of claim 9 wherein the cyclotetrasiloxane has the formula,

$$(R_2^3 SiO)_n$$

where $R^3$ is a monovalent hydrocarbon radical and $n$ varies from 3 to 10.

11. The process of claim 10 wherein the silyl phosphate catalyst concentration is from 1.2 to 60% by weight such as to provide from 0.36% to 0.60% by weight of phosphoric acid equivalency.

12. The process of claim 9 wherein the phosphoric acid equivalency of the silyl phosphate catalyst varies from 1 to 30%.

13. The process of claim 12 wherein the phosphoric acid equivalency of the silyl phosphate catalyst varies from 3 to 20%.

14. The process of claim 9 wherein the reaction period varies from 15 minutes to 2.5 hours.

15. The process of claim 14 wherein the reaction period varies from 30 minutes to 2 hours.

16. The process of claim 14 wherein the reactants are heated such that the reaction temperature is maintained in the range of 90° to 225° C. during the reaction period.

17. The process of claim 9 wherein during the reaction and thereafter the water that is formed is distilled off.

18. The process of claim 1 wherein some of the silyl phosphate catalyst has the formula,

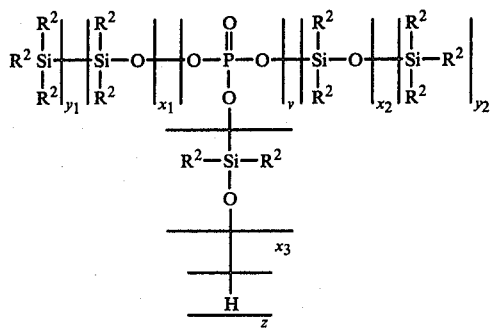

where $v$ is the concentration of the phosphate groups; $y_1 + y_2$ is the concentration of the triorganosiloxy chain-stoppers in the reaction mixture; $x_1 + x_2 + x_3$ is the concentration of diorganosiloxy groups; $z$ is the concentration of hydroxyl groups which may be attached to a silicone or phosphorous atom resulting from incomplete removal of water which concentrations are in the reaction mixture and $R^2$ is a monovalent hydrocarbon radical.

* * * * *